United States Patent [19]
Kroll

[11] Patent Number: 5,944,746
[45] Date of Patent: Aug. 31, 1999

[54] ICD WITH CONTINUOUS REGULAR TESTING OF DEFIBRILLATION LEAD STATUS

[75] Inventor: Mark W. Kroll, Orono, Minn.

[73] Assignee: Pacesetter, Inc., Sylmar, Calif.

[21] Appl. No.: 09/183,263

[22] Filed: Oct. 30, 1998

[51] Int. Cl.⁶ ................................................ A61N 1/37
[52] U.S. Cl. ............................................. 607/27; 607/8
[58] Field of Search ................................. 607/8, 27, 28

[56] References Cited

U.S. PATENT DOCUMENTS

| | | |
|---|---|---|
| 4,899,750 | 2/1990 | Ekwall . |
| 5,076,272 | 12/1991 | Bozidar . |
| 5,534,018 | 7/1996 | Wahlstrand et al. . |
| 5,549,646 | 8/1996 | Katz et al. . |
| 5,755,742 | 5/1998 | Schuelke et al. . |

OTHER PUBLICATIONS

Dohrmann, Mary L. and Goldschlanger, Nora F., "Myocardial Stimulation Threshold in Patients with Cardiac Pacemakers: Effect of Physiologic Variables, Pharmacologic Agents, and Lead Electrodes," *Cardiology Clinics*, pp. 527–537, Nov. 1985.

Clinical Electrophysiology of Pacing, pp. 43–53.

*Primary Examiner*—Scott M. Getzow

[57] ABSTRACT

An implantable cardiac stimulating device which incorporates the functionality of both a pacemaker and an implantable cardioverter-defibrillator (ICD). The implantable cardiac stimulating device is adapted to periodically obtain an impedance measurement by applying a pacing pulse to the pacing tip and measuring the resulting current on a lead connected to one of the high voltage shocking coils implanted within the heart. The measured impedance between the pacing lead and the shocking lead is compared to previously obtained impedance measurements to determine if an increase in the impedance has occurred. The system is further adapted to compare the impedance measurement to the impedance measured between the pacing lead and the casing of the implantable cardiac stimulating device to determine whether any increase in the measured impedance is due to a problem with the pacing lead or a problem with the high voltage coil or high voltage lead.

34 Claims, 5 Drawing Sheets

ICD WITH CONTINUOUS REGULAR TESTING OF DEFIBRILLATION LEAD STATUS

FIELD OF THE INVENTION

The present invention relates to implantable cardiac stimulating devices, and, in particular, to implantable cardiac stimulating devices that incorporate one or more cardioversion or defibrillation leads and further includes a system for periodically assessing the status of the cardioversion or defibrillation leads for damage.

BACKGROUND OF THE INVENTION

Implantable cardiac stimulating devices are devices that are adapted to be implanted within the body of a patient so that therapeutic electrical stimulation can be provided to the patient's heart to regulate heart function. These types of devices include well known pacemakers or implantable cardioverter-defibrillators (ICDs) or devices that include the functionality of both a pacemaker and an ICD. Typically, these devices consist of a control unit having a microprocessor and one or more leads that are adapted to be positioned adjacent the wall of the heart. The control unit generally receives sensory input about the function of the heart and, when the input is indicative of a heart arrhythmia, the control unit then provides an appropriate therapeutic electrical stimulation to the heart via the leads. The therapeutic electrical stimulation can, for example, consist of a low voltage pacing pulse to ensure that the heart is beating correctly or can include a high voltage waveform that is adapted to terminate a particular form of arrhythmia, such as fibrillation.

One particular difficulty with implantable cardiac stimulating devices is that the lead that is adapted to provide the electrical stimulation to the heart can become damaged. In many instances, the leads are implanted into the chambers of the heart. In this environment, the leads are continuously subjected to pressures as a result of the beating of the heart. Over time, the leads can become damaged or even broken such that the delivery of the therapeutic electrical stimulation can be hampered or interrupted.

This can be a particular problem with implantable cardiac stimulating devices that are adapted to terminate more serious forms of arrhythmia. For example, if the implantable cardiac stimulating device is adapted to recognize and provide a therapeutic shock to the heart upon the occurrence of ventricular fibrillation, a broken or damage lead may result in the implantable cardiac stimulating device being unable to provide this waveform. In this case, the ventricular fibrillation may not be corrected and the patient may die. Consequently, it is recognized that the status of the leads that provide the electrical stimulation to the heart must be periodically checked to ensure that the leads are still capable of providing the therapeutic stimulation to the heart.

In fact, it is often recommended that patients who have implanted ICD's periodically have chest x-rays taken so that the status of the leads implanted within the heart can be ascertained. These x-rays can reveal whether a lead is broken, such that the ICD may be unable to provide a therapeutic shock to the heart when the heart experiences a serious arrhythmia. However, using x-rays to assess lead status has several difficulties.

For example, while x-rays may be able to reveal some broken leads, the x-rays may not be able to reveal damage to the leads that would increase the impedance of the lead. An increase in the impedance of the lead may result in the magnitude of the shock being delivered to the heart being degraded such that the shock may be unable to halt the life threatening arrhythmia. Moreover, periodically x-raying patients is expensive and time consuming. Consequently, the x-rays may only be taken at relative long time intervals and the damage to the lead may actually occur in between x-rays. Consequently, some damaged leads may not be detected prior to the lead being called upon to deliver a therapeutic stimulation to the heart to correct a heart abnormality.

To address these particular problems, some implantable cardiac devices of the prior art have instituted procedures whereby the impedance of the leads are periodically measured. Once such example is provided by U.S. Pat. No. 5,549,646 to Katz et al. The device disclosed in this patent included an impedance measurement circuit that has a voltage source which applies a voltage to the ICD leads so that an impedance measurement of the ICD leads can be obtained. The impedance measurement of the ICD leads can then be compared to a reference value to determine whether the lead impedance has exceeded a predetermined amount. One difficulty of the impedance measurement circuit disclosed in U.S. Pat. No. 5,549,646 is that additional circuitry must be provided to the device in order to obtain the impedance measurement.

Moreover, the impedance measurement of the leads is compared to a reference value and this reference value is generally greater than the normal impedance of the lead. Hence, the circuit disclosed in U.S. Pat. No. 5,549,646 is only capable of providing an indication that the lead has been significantly damaged but generally does not provide any indication of small or moderate damage to the lead which results in a small or moderate increase in the lead impedance. Again, moderate damage to the lead may still result in a decrease in the amplitude of a stimulating electrical shock that is to be delivered to the heart which can result in inefficient operation of the implantable cardiac stimulating device or even result in the applied shock being unable to terminate a life threatening arrhythmia.

Another example of a prior art implantable cardiac stimulating device that incorporated circuitry for measuring lead impedance is U.S. Pat. No. 5,755,742 to Schuelke et al. This patent discloses a system whereby the impedance of ICD coils is measured as a result of low voltage pacing pulses being delivered from pacing leads that are implanted within the heart. The pacing pulses are received by the ICD coils such that the impedance of the ICD coil can then be measured. The measured ICD coil impedance is then compared to maximum and minimum impedance values to determine if the ICD coil has experienced a particular problem. However, the device disclosed in U.S. Pat. No. 5,755,742 compares the resulting impedance measurement to maximum and minimum values which are less capable of providing an indication that the lead has suffered small or moderate damage. This problem is compounded by the fact that there is generally not a linear relationship between an impedance of an implanted coil measured at a low voltage and the corresponding impedance of the coil that would occur when a high voltage therapeutic electrical shock is being applied to the heart. Consequently, it is difficult to set minimum and maximum reference values for impedances of leads measured using low voltage pulses that will accurately provide an indication as to whether the lead has experienced some sort of damage that may hinder future delivery of therapeutic waveforms.

Consequently, there is a need for a system which would be capable of measuring the impedance of leads using low voltage pulses that is capable of providing an indication that the lead has experienced damage which could potentially jeopardize the successfully delivery of therapeutic waveforms to the heart to terminate an arrhythmia. To this end, there is a need for a system that is capable of measuring the impedance of the lead at a low voltage and then determining whether the measured impedance is indicative of a possible problem with the lead that requires further analysis.

SUMMARY OF THE INVENTION

The aforementioned needs are satisfied by the implantable cardiac stimulating device of the present invention which comprises a control unit, at least one lead for delivering high energy shock to the heart, and a pacing lead for delivering low voltage pacing pulses to the heart. The control unit is adapted to induce the pacing lead to deliver a pacing pulse where the high voltage lead forms the return path electrode for the pacing pulse. The impedance of the high voltage lead is then measured and the control unit is adapted to compare the measured impedance to previously measured impedance for this high voltage lead. When the measured impedance exceeds the previously measured impedance, the control unit is capable of ascertaining whether the increase in impedance is indicative of damage to the lead.

In one embodiment, the implantable cardiac stimulating device obtains an impedance measurement between a pacing lead and a defibrillation or cardioversion lead and compares the measured impedance with impedance values measured under corresponding conditions during a previous time interval. If the newly measured impedance value exceeds the previously measured impedance value, the implantable cardiac stimulating device is adapted to measure the impedance between the pacing lead and a third electrode so as to be able to compare the impedance between the pacing lead and the cardioversion or defibrillation lead to the impedance between the pacing lead and the third electrode. This comparison will preferably provide an indication as to whether the increase in impedance between the pacing lead and the defibrillation or cardioversion lead is due to damage to the defibrillation or cardioversion lead or is due to damage to or dislodgment of the pacing tip and lead.

In one embodiment, the implantable cardiac stimulating device is adapted to provide an indication to the patient of the increase in the impedance. In particular, the implantable cardiac stimulating device includes an annunciator, such as a piezoelectric beeper or a circuit which provides warning shocks to the patient, that can be actuated upon detecting an increase in the impedance so as to advise the patient of the potentially dangerous situation. The cardiac stimulating device can also be adapted to include a memory and a telemetry circuit so as to allow a position to review the contents of the memory and, in this embodiment, the implantable cardiac stimulating device is further adapted to store data in the memory upon determining that the impedance has increased so that a physician who subsequently reviews the contents of the memory is advised of the increase in the impedance measurement.

The implantable cardiac device of the present invention is capable of measuring the impedances of high voltage leads and is further capable of advising the patient or a treating physician of a potentially dangerous situation. Since the measurements in the preferred embodiment are conducted during corresponding conditions, a variation in the received impedance measurement is typically indicative of a potential problem. Hence, the implantable cardiac stimulating device in the preferred embodiment more sensitive than systems of the prior art and is capable of detecting a potential problem, such as a broken, damaged or dislodged lead, using a low voltage pacing pulse. Since the measurements are obtained in corresponding conditions the resulting impedance measurements can be compared to previously obtained measurements which can provide an indication as to problems with leads that are less than a very serious problem with the lead. These and other objects and advantages of the present invention will come more apparent from the following description taken in conjunction with the accompanying drawings.

DETAILED DESCRIPTION OF THE PREFERRED EMBODIMENT

Figure 1:
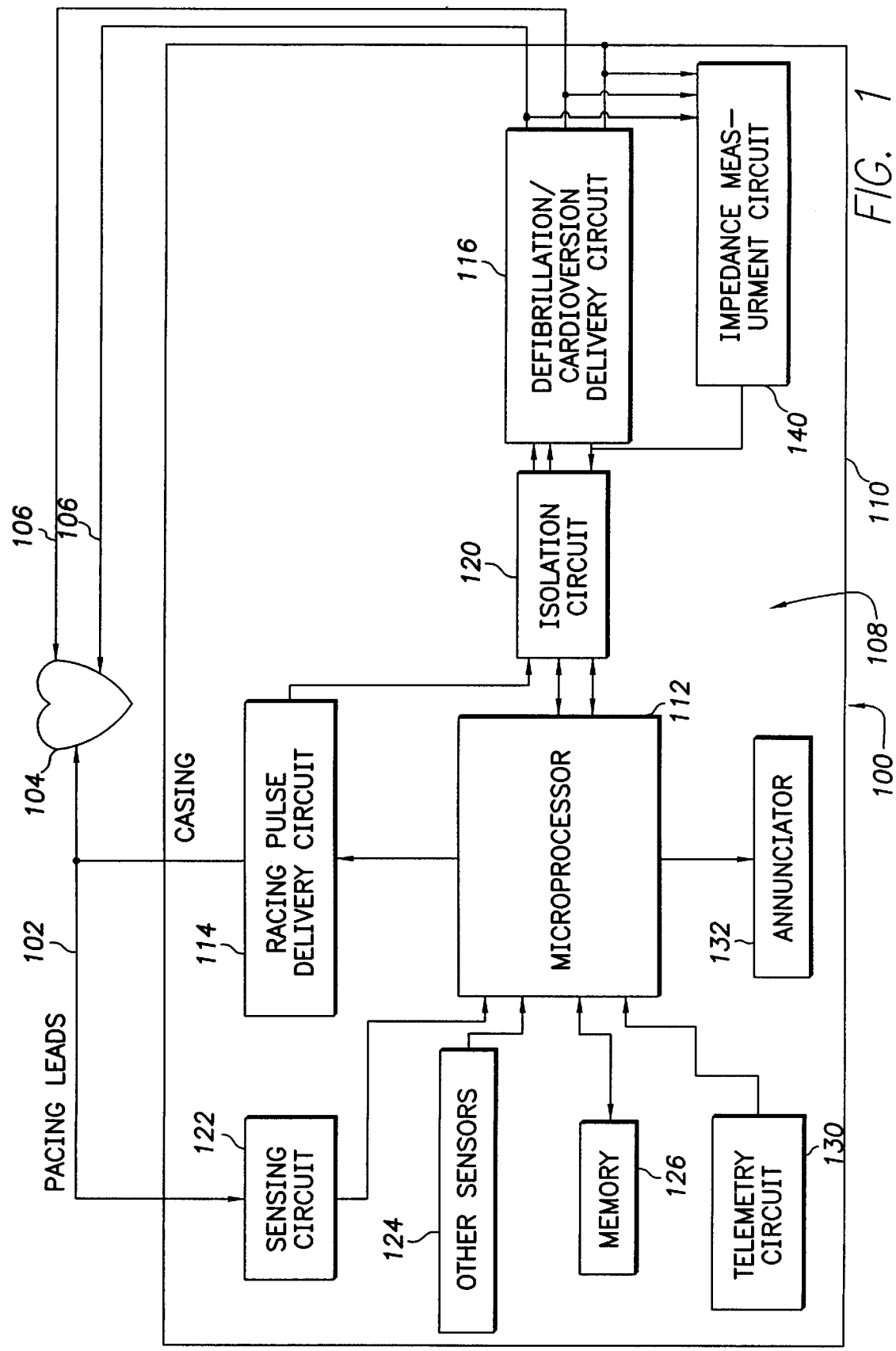
FIG. 1 is a simplified block diagram of one embodiment of an implantable cardiac stimulating device incorporating the impedance measurement circuit of the preferred embodiment.
Figure 2:
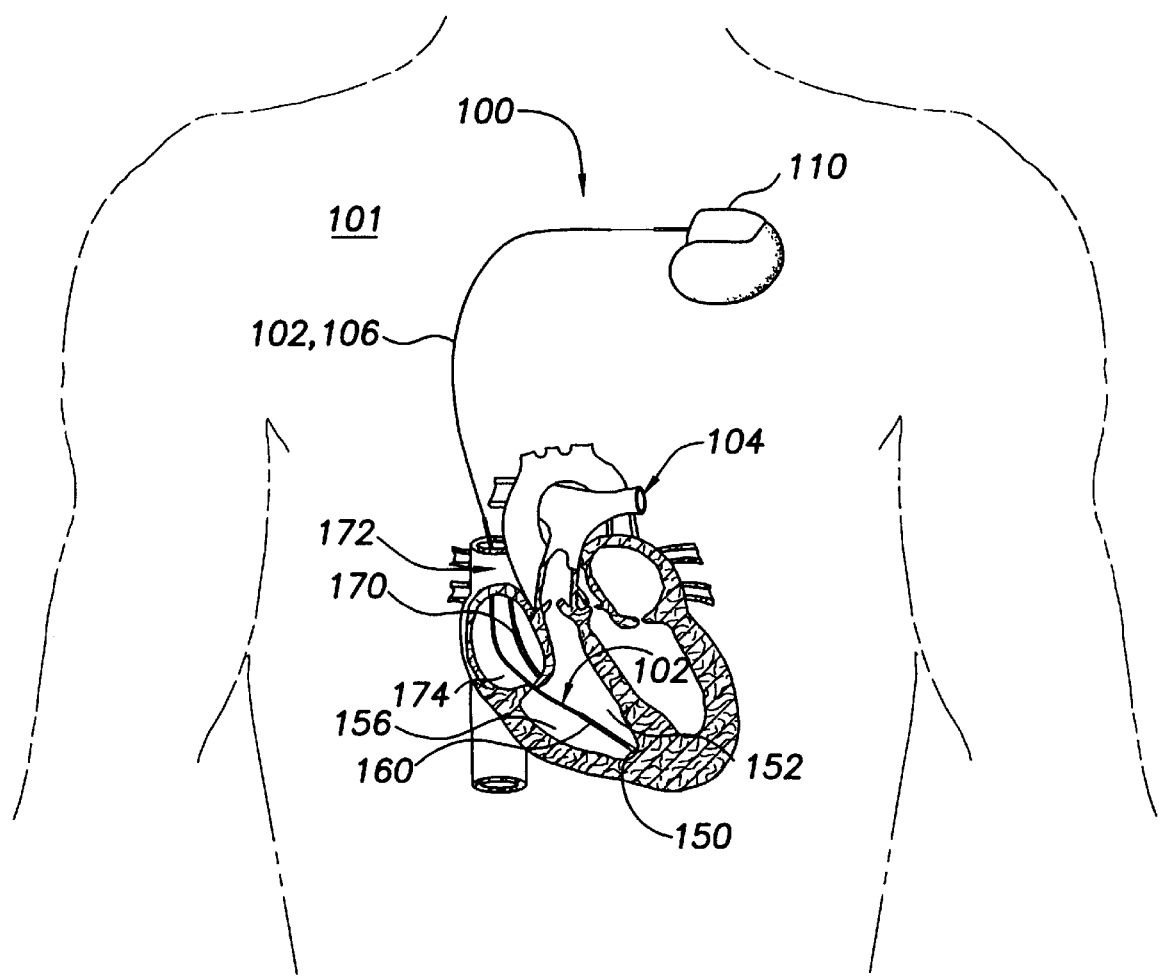
FIG. 2 is a diagram illustrating the implantable cardiac stimulating device of FIG. 1 as it is implanted in a patient.

Reference will now be made to the drawings wherein like numerals referred like parts through out. FIG. 1 is a block diagram of an exemplary implantable cardiac stimulating device 100 of the preferred embodiment. In particular, the implantable cardiac stimulating device 100 is capable of providing both pacing pulses and higher voltage waveforms such as cardioversion or defibrillation waveforms. In particular, the implantable cardiac stimulating device 100 has one or more pacing leads 102 that are adapted to be positioned adjacent the heart 104 in a position where the delivery of pacing pulses will result in a paced beat response of a chamber of the heart. One typical place for the location of the tip of the pacing leads is in the apex of the right ventricle of the heart 104 as shown in FIG. 2. Similarly, the implantable cardiac stimulating device 100 also include one or more high voltage leads 106 that are adapted to supply either cardioversion or defibrillation waveforms to the heart 104 in a manner that is known in the art. The high voltage leads 106 typically terminate in coils that are implanted in various locations within the heart 104, such as the right ventricle or the superior vena cava, that are selected so that the delivery of a high voltage waveform will terminate a tachycardia or fibrillation episode of the heart 104. The placement of exemplary pacing leads 102 and high voltage coil will be described in greater detail in reference to FIGS. 2 and 3 herein below.

The implantable cardiac stimulating device also incorporates a control unit 108 that is positioned within a casing 110. The control unit 108 incorporates the control circuitry that is adapted to deliver either the pacing pulses or the high voltage waveforms to the heart via the leads 102 or 106 respectively. In this embodiment, the control unit incorporates a microprocessor 112 that is adapted to induce the delivery of the pacing pulses via a pacing pulse delivery circuit 114 in the pacing leads 102 in a manner that is known in the art. Similarly, the microprocessor 112 is adapted to induce a defibrillation-cardioversion delivery circuit 116 to supply an appropriate high voltage, e.g. 200–300 volts peak to peak, waveform via the high voltage leads 106 to terminate a tachycardia or fibrillation also in a manner that is known in the art. As is also shown in FIG. 1, the high voltage defibrillation-cardioversion delivery circuit 116 is typically isolated from the low voltage microprocessor 112, the sensors 122–126, and the pacing pulse delivery circuit 114 via an isolation circuit 120. The configuration of the isolation circuit 120 can be any of a number of configurations known in the art.

The microprocessor 112 induces the pacing pulse delivery circuit 114 or the defibrillation cardioversion delivery circuit 116 to provide the appropriate waveforms based upon inputs from various sensors. In particular, the microprocessor 112 receives a sensor input which is indicative of the activity of the heart from a sensing circuit 122. In this embodiment, the sensing circuit 122 is connected to the pacing leads 102 such that the pacing leads 102 can provide an intracardiac electrogram (IEG) to the microprocessor in a manner that is known in the art. In this way, the microprocessor 112 can receive a signal that is indicative of the actual heart function. The microprocessor 112 is adapted to interpret the signal to recognize various cardiac arrhythmias so that the microprocessor 112 can induce an appropriate stimulation from either the pacing pulse delivery circuit 114 or the defibrillation-cardioversion delivery circuit 116 in a manner that is generally known in the art. The microprocessor 112 may also receive signals from other sensors 124, such as acceleration sensors, minute ventilation sensors and the like so that the microprocessor 112 is able to optimize the delivery of pacing pulses or high voltage defibrillation-cardioversion waveforms to the heart 104.

The control unit 108 in this embodiment also incorporates a memory 126 that contain both operating instructions for the microprocessor 112 and can also contain data that is recorded in the memory 126 by the microprocessor 112. In this embodiment, the data can preferably be subsequently accessed by a treating physician via a telemetry circuit 130 in a manner that is known in the art. The data that is stored within the memory 126 for subsequent access by a treating physician may include operating parameters of the implantable cardiac device 100 or observed patient parameters, e.g., responses to particular waveforms, etc.

In this embodiment, the control unit 108 also incorporates an annunciator 132 that can be activated by the microprocessor 112 so as to provide the patient with a warning. In this embodiment, the annunciator 132 can be comprised of a piezoelectric buzzer that will emit an audible tone to the patient or can further comprise circuitry that will enable the microprocessor 112 to induce the delivery of shocks to the patient that will alert the patient to the existence of a particular problem without stimulating the heart 104. Alternatively, an annunciator function may also comprise storing data in the memory indicative of the problem so that a treating physician can subsequently review the data.

Each of the components of the implantable cardiac stimulating device 100 is powered by a battery (not shown). The use of a limited power supply such as a battery to power the device 100 imposes significant design constraints on the implantable cardiac stimulating device 100. For example, it is generally desirable to limit the consumption of battery power for sensory measurements to preserve the operational longevity of the device.

This embodiment of the control unit 108 also incorporates an impedance measurement circuit 140 that is adapted to measure the impedance of the high voltage leads 106 to determine whether the impedance of the high voltage leads 106 is indicative of a particular problem with these leads. As will be discussed in greater detail below, the microprocessor 112 is adapted to induce the pacing pulse delivery circuit 114 to provide a pacing pulse via the pacing leads 102 and simultaneously induce the impedance measurement circuit 140 to enable a particular high voltage lead 106 so as to be able to measure the current that is flowing between the pacing lead 102 and the selected high voltage lead 106. This measurement provides an indication of the impedance of the high voltage lead 106. In this way, a low voltage, low power signal, e.g., on the order of 3–5 volts, can be applied to the high voltage leads 106 and the resulting impedance can be measured without requiring that additional circuitry be implanted within the control unit 108. Moreover, the use of a low voltage pacing pulse 102 reduces the drain on the battery during determination of high voltage lead impedance.

As was discussed in greater detail above, it is desirable to be able to determine the impedance of the high voltage lead as a rise in the impedance of the high voltage lead 106 may be indicative of a problem with the lead that could inhibit the delivery of successful cardioversion or defibrillation waveforms to the heart to terminate a cardiac arrhythmia. In fact, a rise in the measured impedance of the high voltage lead 106 may be indicative of a broken lead or a damaged lead such that the implantable cardiac stimulating device 100 may be incapable of terminating a life threatening arrhythmia. As will be discussed in greater detail below, the microprocessor 112 is adapted so that upon the detection of a rising lead impedance, which is indicative of damage to the high voltage lead 106, the microprocessor 112 induces the annunciator 132 to provide an appropriate signal to the patient to thereby indicate to the patient of the existence of a potentially dangerous situation to provoke the patient to seek further medical treatment from a physician.

FIG. 2 illustrates one configuration of the implantable cardiac stimulating device 100 as it is implanted within the body of a patient 101. Specifically, in this embodiment, the casing 110 of the implantable cardiac stimulating device 100 is implanted within the body of the patient under the pectoral muscle of the patient 101 in a manner that is known in the art. The leads 102, 106 are inserted into a vein, such as the subclavian vein and the leads 102, 106 are guided into the right atrium 174 and the right ventricle 156 in the manner shown in FIG. 2. In this embodiment, the pacing lead 102 terminates in a pacing tip 150 that is implanted adjacent the apex 152 of the right ventricle 156 of the heart 104. The high voltage leads 106 terminate in an RV shocking electrode or coil 160 that is positioned within the right ventricle 156 of the heart 104 and into an SVC shocking electrode or coil 170 that is positioned within the subvena cava 172 of the heart 104 adjacent the right atrium 174 of the heart 104. The implantation of the pacing tip 150, the RV shocking coil 160 and the SVC shocking coil 170 are accomplished in a manner that is generally known in the art. The pacing tip 150 is adapted to delivering pacing pulses to the apex 152 of the right ventricle 156 to induce a paced beat response of the heart 104. Both the RV coil 160 and the SVC coil 170 are adapted to provide high voltage waveforms to the heart so as to terminate cardiac arrhythmias, such as ventricular fibrillation or atrial fibrillation.

The implantable cardiac stimulating device 100 of this embodiment is adapted to deliver pacing pulses from the pacing tip 150 to either the RV coil 160 or the SVC coil 170 so that the resulting current on the RV coil 160 and the SVC coil 170 can be measured. This measurement provides an indication of the impedance of the RV coil 160 or the SVC electrode 170 and the associated high voltage leads 106. It will, however, be appreciated that the measured impedance has several components including the impedance of the pacing tip 150 as it is implanted in the apex 152 of the right ventricle 156, the impedance of the blood between the pacing tip 150 and the coil 160, 170 to be measured, the impedance of the selected high voltage coil 160 or 170 and the impedance of the associated high voltage lead 106. As it is desirable to determine whether there has been an increase in the component of the total measure impedance that is attributable to the coil 160 or 170 or the associated lead 106, it is generally desirable to provide the pacing pulse at approximately the same condition so that the variation of the impedance between two measurements due to the action of the heart 104 can be discounted.

Figure 3:
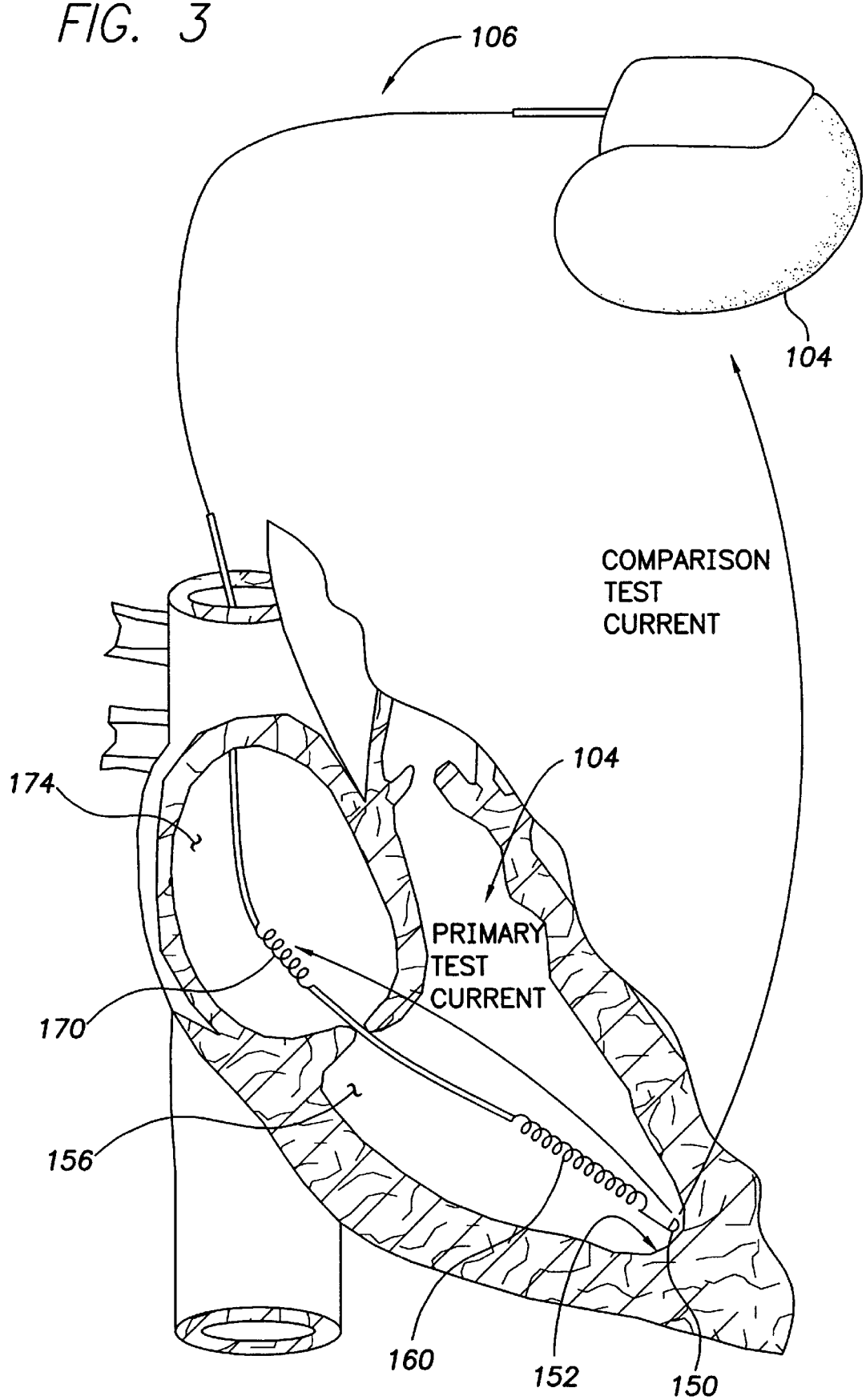
FIG. 3 is a schematic diagram illustrating the measurement path of the impedance measurement circuit of the implantable cardiac stimulating device of FIG. 1.

FIG. 3 is a schematic illustration of the implantable cardiac stimulating device 100 as it measure the impedances of one of the high voltage leads 106 and associated coil 160, 170, and initiates a compare routine to determine whether the impedance measurement indicates the existence of a potential problem with the high voltage lead 106. As will be explained in greater detail below, the implantable cardiac stimulating device 100 initially provides a pacing pulse from the pacing tip 150 to the coil, either coil 160 or coil 170 that is to be measured. The microprocessor 112 selects the coil 160, 170 and the associated lead 106 to be measured by sending an appropriate signal to the impedance measurement circuit 140 (FIG. 1) to configure the selected coil 160, 170 and the associated lead 106 as the return electrode for the pacing pulse. This measurement is taken during a preselected period of the cardiac cycle and the measurement is compared to previously obtained measurements under similar circumstances for the particular coil 160, 170. In the event that the measured impedance exceeds the previously measured impedance, there is the possibility that the coil 160, 170 or the high voltage leads 106 or even the pacing lead 102 has become damaged or dislodged to thereby increase the measured impedance.

In one embodiment, the microprocessor 112 is adapted to measure the impedance between the pacing lead 102 and the casing 110 in the event that the impedance measured between the pacing lead 102 and the coil 160, 170 and associated lead 106 under test exceeds a previously recorded impedance measurement for the particular coil 160, 170 and lead 106. This is accomplished by the microprocessor 112 sending a signal to the impedance measurement circuit 140 to configure the casing 110 as the return electrode and while simultaneously inducing the pacing pulse delivery circuit 114 to deliver the low voltage test pulse via the pacing lead 102 and the pacing tip 150. The measured current returning to the casing 110 is indicative of the impedance between the pacing tip 150 and the casing 112. The microprocessor 112 then compares the new impedance measurement between the pacing lead 102 and the coil 160, 170 and associated lead 106 to the impedance measured between the pacing lead 102 and the casing 110. This measurement can be used to determine whether the increase in the measured impedance between the pacing lead 102 and the coil 160, 170 is the result of damage to the selected coil 160, 170 or the associated high voltage lead 106 or is the result of dislodgment of or damage to the pacing lead 102 or tip 150.

It will be appreciated that in the event that the pacing lead 102 or tip 150 has become damaged or dislodged, the impedance between the pacing lead 102 and the casing 110 will be greater than the impedance between the pacing lead 102 and the coil 160, 170 and the associated lead 106. While dislodgment of the pacing tip 150 can be a problem for the patient, it is generally not as serious of a problem as an increase in the impedance of the coil 160, 170 and associated lead 106 which could be indicative of damage to the coil 160, 170 or the high voltage leads 106 which would inhibit the implantable cardiac stimulating device 100 from providing an appropriate therapeutic shock to terminate a potentially life threatening arrhythmia. Hence, being able to discriminate between an impedance measurement that is indicative of damage to the pacing lead 102 or dislodgment of the pacing tip 150 and an impedance measurement which is indicative of a potential problem with the high voltage lead or coil, is particularly beneficial for ensuring that the patient seeks appropriate follow-up care.

Figure 4A:
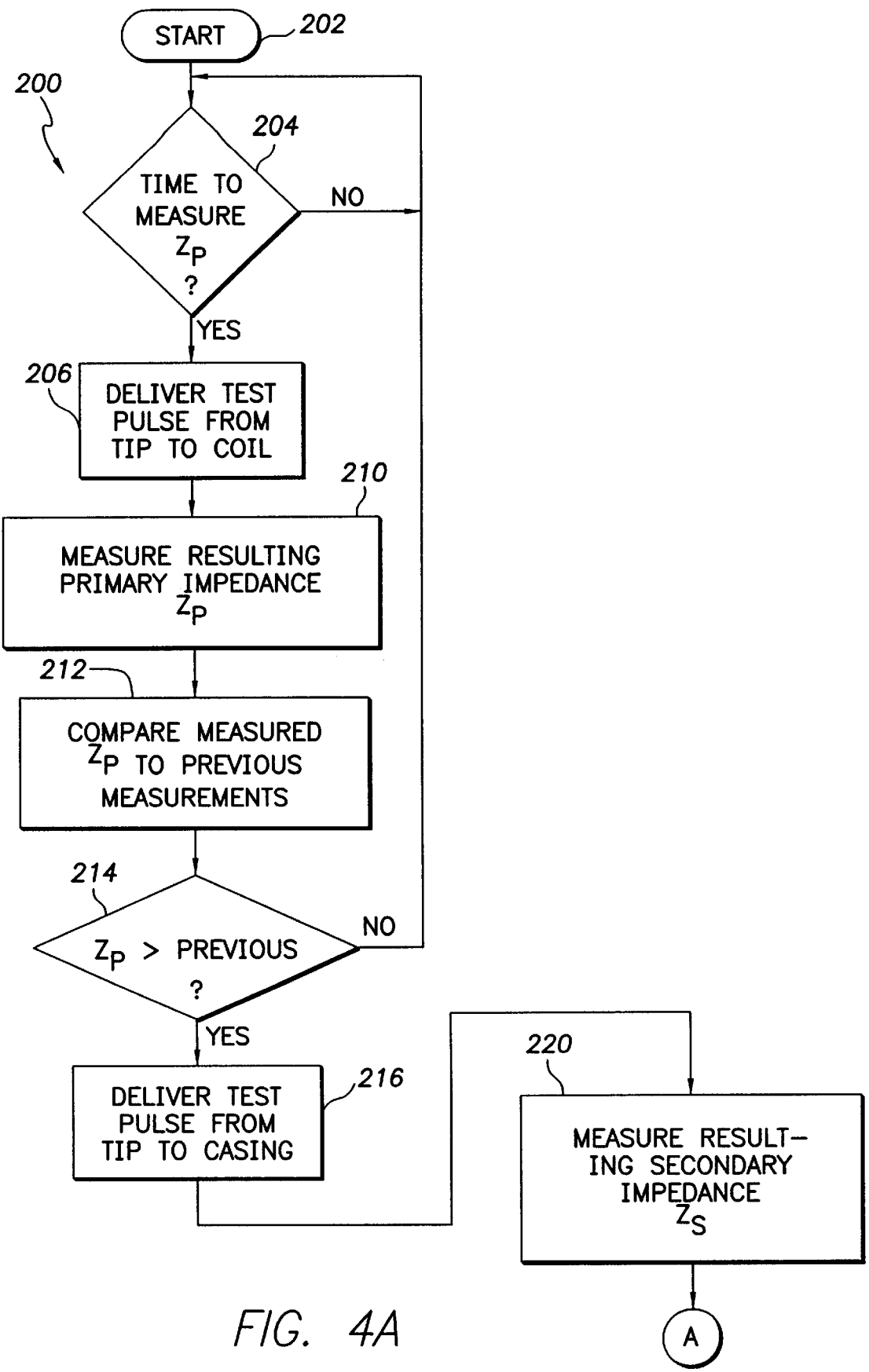
FIGS. 4a, 4b is a flowchart which illustrate the operation of the implantable cardiac stimulating device of FIG. 1 while performing an impedance measurement on a lead of the implantable cardiac device.
Figure 4B:
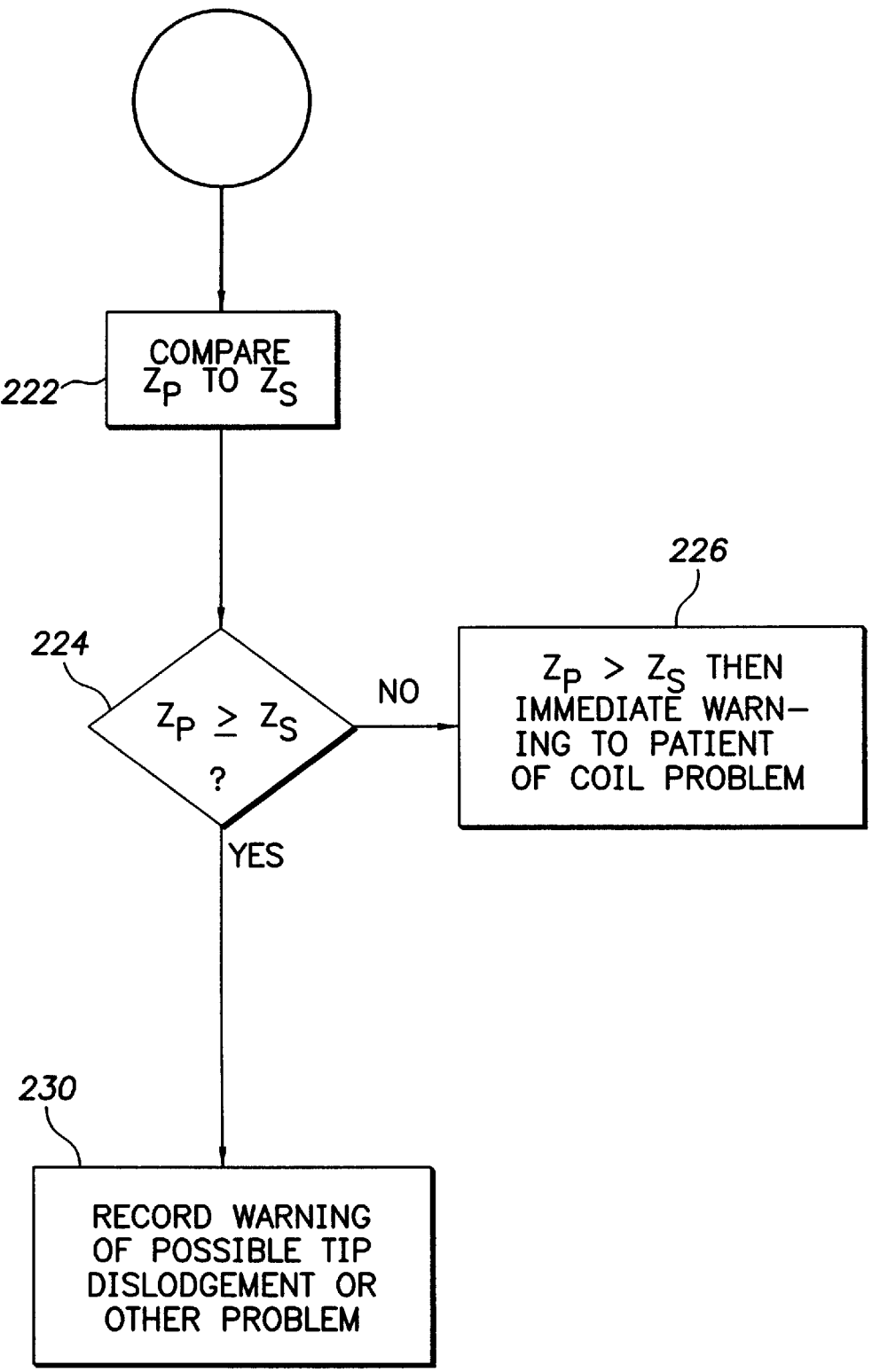

FIGS. 4a, 4b is an exemplary flowchart which illustrates the operation of the implantable cardiac stimulating device 100 as it performs the impedance measurement in comparison process 200 of the preferred embodiment. In particular, the microprocessor 112, from a start state 202, initially determines in decision state 204 whether the time period for measuring the impedance between the pacing lead 102 and the selected high voltage coil and lead has occurred. In particular, the microprocessor 112 is adapted to periodically measure, (e.g. once a day), the impedance $Z_p$ between the pacing lead 102 and a selected high energy coil, either the RV coil 160 or the SVC coil 170 and the associated lead 106 in the embodiment shown in FIG. 2. If the microprocessor 112 determines in decision state 204 that the time to measure the impedance $Z_p$ between the pacing lead 102 and the selected coil 160, 170 and associated lead 106 has occurred, the microprocessor 112 then induces, in state 206, the pacing pulse delivery circuit 114 to deliver a low voltage test pulse of known magnitude and duration from the pacing tip 150 to the selected coil 160, 170.

Preferably, the microprocessor 112 is adapted to induce the pacing pulse delivery circuit 114 to provide the test pulse, which is preferably a known pacing pulse, at a time when the delivery of the test pulse is not likely to induce a paced beat response of the heart 104. Moreover, the microprocessor 112 may delay the delivery of the pacing tip in state 206 until the sensed condition of the operation of the heart 104 from the sensing circuit 122 and the other sensors 124 correspond to the same sensed conditions of previously obtained impedance measurements $Z_p$ so as to reduce the probability that a changed condition in the heart 104 will result in a significantly different measurement of the impedance $Z_p$.

While inducing the delivery of the low voltage test pulse in state 206, the microprocessor 112 is also simultaneously inducing the impedance measurement circuit 140 to configure the lead 106 associated with the selected coil 160, 170 as the return electrode for the test pulse so that the current that occurs on the selected lead 106 is measured in state 210. Knowing the magnitude and duration of the test pacing pulse that is provided in state 206 and the measured current obtained by the impedance measurement circuit 140 in state 210 results in the microprocessor 112 receiving, in state 210, a signal from the impedance measurement circuit 140 that is indicative of the primary impedance $Z_p$ between the pacing lead 102 and the lead 106 corresponding to the selected coil 160, 170.

The microprocessor 112 then stores the impedance measurement $Z_p$ in the memory 126 and compares, in state 212, the measured $Z_p$ value to previously obtained measurements of the impedance $Z_p$ between the pacing lead 102 and the lead 106 corresponding to the selected coil 160, 170 that are stored in the memory 126 of the implantable cardiac stimulating device 100. Again, as discussed above, the impedance measurement $Z_p$ is preferably obtained under essentially the same conditions of the heart 104 as previous measurements so that the primary contribution to a change in the measured impedance $Z_p$ is the result of an increase in the impedance of either the selected coil 160, 170, the corresponding lead 106 or the impedance of the pacing lead 102 or the pacing tip 150.

The microprocessor 112 then determines in decision state 214 whether the impedance measurement $Z_p$ is greater than previously obtained impedance measurements. If the newly obtained impedance measurement $Z_p$ is less than or equal to the previously obtained measurement, obtained under corresponding conditions, then there has not been any change in the impedance of the coil 160, 170 or the leads 106 that would inhibit the desired operation of the implantable cardiac stimulating device 100 in delivering high voltage therapeutic waveforms to the heart 104 to terminate arrhythmias. In this case the microprocessor 112 returns to the start state 202 and waits for the next time interval to obtain the $Z_p$ measurement.

Alternatively, if the impedance $Z_p$ between the pacing lead 102 and the selected coil 160, 170 and the associated lead 106 has increased over impedance measurements previously obtained under similar circumstances, then there is reason to believe that a condition has occurred during the interval between the impedance measurements that is affecting the impedance measurement value. The condition that may have occurred can include damage to the high voltage coil 160, 170, damaged to the associated high voltage leads 106, damage to the pacing lead 102 or dislodgment of the pacing tip 150.

In order to determine whether the increase in impedance is the result of potential damage to the high voltage leads 106 or the high voltage coil 160, 170 or whether the increase in the impedance is the result of damage to or dislodgment of the pacing lead 102 or tip 150, the microprocessor 112 then induces the pacing pulse delivery circuit 114 to deliver, in state 216, a pacing pulse from the tip 150 to the casing 110. In this circumstance, the casing 110 is coupled to the impedance measurement circuit 140 so that the casing 110 is a passive electrode that receives current in response to a test pulse being delivered by the pacing pulse delivery circuit 114 via the pacing lead 102 and the tip 150. Hence, the microprocessor 112 can then receive a secondary impedance measurement $Z_s$ in state 220 that is indicative of the impedance between the pacing lead 102 and the casing 110.

The microprocessor 112 then compares, in state 222, the impedance measurement $Z_p$ measured between the pacing lead 102 and the lead 106 corresponding to the selected coil 160, 170 to the impedance measurement $Z_s$ between the pacing lead 102 and the casing 110. The microprocessor 112 then determines in decision state 224 whether the impedance $Z_s$ between the pacing lead 102 and the casing 110 is greater than or equal to the impedance $Z_p$ between the pacing lead 102 and the lead 106 corresponding the selected coil 160, 170. If the impedance measurement $Z_s$ is greater than or equal to the impedance measurement $Z_p$, then the microprocessor 112 determines that the increase in the impedance $Z_p$ from the previously obtained $Z_p$ measurement is likely the result of a pacing tip dislodgment, pacing lead damage or some other problem. Consequently, the microprocessor 112 then records in the memory 126 an indication that the pacing tip 150 may have become dislodged, the pacing lead 102 may be damaged or that some other problem may have occurred which increased the impedance. A treating physician can then be provided an indication of the particular problem when accessing the data in the memory 126 via the telemetry circuit 130 on a subsequent follow-up doctor visit in a manner that is known in the art.

However, if the impedance measurement $Z_p$ between the pacing lead 102 and the lead 106 corresponding to the selected coil 160, 170 is greater than the impedance $Z_s$ measured between the pacing lead 102 and the casing 110, then the increase of impedance is likely to be the result of either damage to the coil 160, 170 or damage to the corresponding lead 106. In this embodiment, the microprocessor 112 is adapted to induce the annunciator 132 (FIG. 1) to provide an immediate warning in state 226 to the patient that is indicative of a potential lead problem. This immediate warning provided by the annunciator 132 may be in the form of an audible tone that the patient can hear or in the form of a non-therapeutic electrical stimulation that is provided to the patient that will stimulate sensory nerves without stimulating cardiac nerves.

It will be appreciated that the implantable cardiac stimulating device 100 of the preferred embodiment is capable of detecting increases in impedance using low power pacing pulses. The use of low power pacing pulses to measure impedance conserves energy and also minimizes the discomfort experienced by the patient. However, because the system of the preferred embodiment is comparing the resulting low voltage impedance measurement to previously recorded impedance measurements obtained under similar conditions, an increase in the impedance that would occur when a high voltage therapeutic shock is delivered to the heart is detected with greater sensitivity than with prior art systems.

In particular, the system of the preferred embodiment detects very small increases in impedance measured at low voltages and can provide a signal indicative thereof without requiring that the impedance exceed a pre-selected threshold. Hence, the system of the preferred embodiment is capable of providing an indication of conditions that may result in significant increases in the impedance when a high voltage waveform is applied that would not otherwise be detected by prior art systems.

Moreover, the system of the preferred embodiment is also capable of distinguishing between increases in impedances that are due to more serious conditions from less serious conditions. In particular, the system of the preferred embodiment is capable of distinguishing between increases in impedances that could occur as a result of damage to or dislodgment of the pacing tip from increases in impedances that could be the result of damage to either the high voltage shocking coils or the high voltage leads connected to the high voltage shocking coils. Hence, the system of the preferred embodiment is more capable of measuring small changes in impedance measured at low voltages which may correspond to various significant changes in impedances measured at high voltages and then further ascertaining the causation of such changes and impedances.

Although the preferred embodiment of the present invention has shown, described and pointed out the fundamental novel features of the invention as applied to this embodiments, it will be understood that various omissions, substitutions and changes in the form of the detail of the device illustrated may be made by those skilled in the art without departing from the spirit of the present invention. Consequently, the scope of the invention should not be limited to the foregoing description, but should be defined by the appending claims.

What is claimed is:

1. An implantable cardiac stimulating device comprising:

means for delivering pacing pulses to the heart of a patient;

means for delivering high voltage therapeutic waveforms to the heart of a patient;

impedance measuring means for selectively obtaining a first impedance measurement between the means for delivering pacing pulses to the heart of a patient and the means for delivering high voltage therapeutic waveforms to the heart of the patient;

control means for controlling the delivery of pacing pulses and high voltage therapeutic waveforms to the heart of the patient and for controlling the impedance measuring means wherein the control means is adapted to periodically induce the impedance measuring means to obtain the first impedance measurement and wherein the control means compares the first impedance measurement to previously obtained first impedance measurements; and annunciator means for providing the patient with a warning when the control means determines that the first impedance measurement exceeds previously obtained first impedance measurements.

2. The device of claim 1, wherein the means for delivering pacing pulses to the heart of a patient comprises a pacing lead and tip adapted to be implanted within the heart of the patient.

3. The device of claim 1, wherein the means for delivering high voltage therapeutic waveforms to the heart of the patient comprises a high voltage lead and a coil that are adapted to be implanted within the heart of a patient.

4. The device of claim 1, wherein the control means includes a microprocessor with an associated memory and the microprocessor is adapted to record the first impedance measurements in the memory.

5. The device of claim 4, wherein the microprocessor periodically induces the means for delivering pacing pulses to the heart to deliver a low voltage test pulse and wherein the microprocessor simultaneously induces the impedance measurement means to measure the electrical response on the means for delivering high voltage therapeutic waveforms to the heart of the patient occurring as a result of the delivery of the low voltage test pulse to thereby obtain the first impedance measurement.

6. The device of claim 5, further comprising an indifferent electrode that is adapted to be implanted within the body of the patient.

7. The device of claim 6, wherein the impedance measuring means is further adapted for obtaining a second impedance measurement between the means for delivering pacing pulses to the heart of a patient and the indifferent electrode.

8. The device of claim 7, wherein the microprocessor induces the impedance measuring means to obtain the second impedance measurement upon determining that the first impedance measurement exceeds previously obtained first impedance measurements.

9. The device of claim 8, wherein the microprocessor compares the first impedance to the second impedance and activates the annunciator means only upon determining that the first impedance measurement is greater than the second impedance measurement thereby indicating that the impedance of the means for delivering high voltage therapeutic waveforms to the heart of the patient has increased so as to provide an indication that the means for delivering the high voltage therapeutic waveform has been damaged.

10. The device of claim 9, wherein the microprocessor induces the means for delivering pacing pulses to the heart of the patient to deliver the low voltage test pulse and the microprocessor simultaneously induces the impedance measurement means to measure the electrical response resulting from the delivery of the low voltage test pulse on the indifferent electrode to obtain the second impedance measurement.

11. The device of claim 10, wherein the low voltage test pulse is comprised of a pacing pulse.

12. The device of claim 10, wherein the annunciator means is comprised of a piezoelectric annunciator that provides an audible signal to the patient upon activation of the annunciator means by the control means.

13. An implantable cardiac stimulating device comprising:

a pacing lead adapted to be implanted in the body of a patient so as to be able to provide pacing pulses to the heart of the patient;

a high voltage lead adapted to be implanted in the body of a patient so as to be able to provide high voltage cardioversion or defibrillation waveforms to the heart of the patient;

a control unit, adapted to be implanted in the body of the patient, the control unit being further adapted to periodically induce the pacing lead to emit a first pacing pulse and wherein the control unit is further adapted to measure the resulting electrical response occurring on the high voltage lead so as to be able to obtain a first impedance measurement, wherein the control unit records the first impedance measurement in a memory associated with the control unit and wherein the control unit compares the first impedance measurement to previously obtained first impedance measurements and provides an indication of a potential problem in the high voltage lead when the first impedance measurement exceeds previously obtained first impedance measurements.

14. The device of claim 13, further comprising an indifferent electrode that is adapted to be implanted within the body of the patient.

15. The device of claim 14, wherein the control unit, upon obtaining a first impedance measurement that exceeds previously recorded first impedance measurements, induces the pacing lead to emit the first pacing pulse and wherein the control unit measures the resulting electrical response occurring on the indifferent electrode so as to obtain a second impedance measurement.

16. The device of claim 15, further comprising an annunciator and the control unit enables the annunciator upon obtaining a first impedance measurement that is greater than the previously recorded first impedance measurements and is also greater than the second impedance measurement so that the patient is advised of the need to seek follow up care for a possibly damaged high voltage lead.

17. The device of claim 16, wherein the annunciator is comprised of a piezoelectric element that is adapted to be implanted within the body of the patient and wherein the piezoelectric element emits an audible tone to advise the patient of the need to seek follow up care for the possibly damaged high voltage lead.

18. The device of claim 15, the memory associated with the control unit is adapted to be accessible by a treating physician via a telemetry link so that the treating physician can review stored data including the stored first impedance measurements.

19. The device of claim 18, wherein the control unit is adapted to store a warning in the memory after obtaining a first impedance measurement that is greater than previously recorded first impedance measurements but is less than the second impedance measurement so that a treating physician who is subsequently reviewing the contents of the memory can be advised of a potential pacing tip dislodgement or pacing lead damage.

20. The device of claim 14, wherein the indifferent electrode is comprised of a casing that contains the control unit.

21. The device of claim 13, wherein the high voltage lead is comprised of an RV electrode that is adapted to be implanted within the right ventricle of the heart to deliver defibrillation waveforms to the heart.

22. The device of claim 13, wherein the high voltage lead is comprised of a sub-vena cava electrode that is adapted to be implanted within the sub vena cava of the patient's heart to deliver cardioversion waveforms to the heart.

23. An implantable cardiac stimulating device comprising:
   a pacing lead adapted to be implanted in the body of a patient so as to be able to provide pacing pulses to the heart of the patient;
   a high voltage lead adapted to be implanted in the body of a patient so as to be able to provide high voltage cardioversion or defibrillation waveforms to the heart of the patient;
   an indifferent electrode that is adapted to be implanted within the body of the patient; and
   a control unit, adapted to be implanted in the body of the patient, the control unit being further adapted to periodically induce the pacing lead to emit a first pacing pulse and wherein the control unit is further adapted to measure the resulting electrical response occurring on the high voltage lead so as to be able to obtain a first impedance measurement, wherein the control unit records the first impedance measurement in a memory associated with the control unit and wherein the control unit compares the first impedance measurement to previously obtained first impedance measurements and is adapted to further induce the pacing lead to emit a second pacing pulse and measure the resulting electrical response occurring on the indifferent electrode so as to be able to obtain a second impedance measurement and wherein the control unit is further adapted to provide an indication of a potential problem in the high voltage lead when the first impedance measurement exceeds previously obtained first impedance measurements and the second impedance measurement.

24. The device of claim 23, further comprising an annunciator and the control unit enables the annunciator upon obtaining a first impedance measurement that is greater than the previously recorded first impedance measurements and is also greater than the second impedance measurement so that the patient is advised of the need to seek follow up care for a possibly damaged high voltage lead.

25. The device of claim 24, wherein the annunciator is comprised of a piezoelectric element that is adapted to be implanted within the body of the patient and wherein the piezoelectric element emits an audible tone to advise the patient of the need to seek follow up care for a possibly damaged high voltage lead.

26. The device of claim 25, the memory associated with the control unit is adapted to be accessible by a treating physician via a telemetry link so that the treating physician can review stored data including the stored first impedance measurements.

27. The device of claim 26, wherein the control unit is adapted to store a warning in the memory after obtaining a first impedance measurement that is greater than previously recorded first impedance measurements but is less than the second impedance measurement so that a treating physician who is subsequently reviewing the contents of the memory can be advised of a potential pacing tip dislodgment or pacing lead damage.

28. The device of claim 23, wherein the indifferent electrode is comprised of a casing that contains the control unit.

29. The device of claim 23, wherein the high voltage lead is comprised of an RV electrode that is adapted to be implanted within the right ventricle of the heart to deliver defibrillation waveforms to the heart.

30. The device of claim 23, wherein the high voltage lead is comprised of a sub-vena cava electrode that is adapted to be implanted within the sub vena cava of the patient's heart to deliver cardioversion waveforms to the heart.

31. A method of assessing the impedance of leads of an implanted cardiac stimulating device, the method comprising:
   emitting a first pacing pulse from a pacing tip implanted in the heart of a patient;
   measuring the resulting electrical response on a high voltage lead implanted in the heart of a patient;
   determining a first impedance measurement indicative of the impedance of the high voltage lead;
   comparing the first impedance measurement to previously obtained first impedance measurements; and
   warning the patient of the existence of a potential problem with the high voltage lead when the first impedance measurement exceeds previously obtained first impedance measurements for the high voltage lead.

32. The method of claim 31, further comprising:
   emitting a second pacing pulse form the pacing tip implanted in the heart of a patient when the first impedance measurements exceeds previously obtained first impedance measurements;
   measuring the resulting electrical activity on a third electrode so as to obtain a second impedance measurement.

33. The method of claim 32, wherein warning the patient of the existence of a potential problem of the lead occurs only when the first impedance measurement exceeds the previously obtained first impedance measurements for the high voltage lead and further exceeds the second impedance measurement.

34. The method of claim 33, wherein the step of warning the patient comprises activating an annunciator so as to produce an audible tone.

* * * * *